US011746341B2

(12) United States Patent
Degering et al.

(10) Patent No.: US 11,746,341 B2
(45) Date of Patent: Sep. 5, 2023

(54) PERFORMANCE-ENHANCED AND STORAGE STABLE PROTEASE VARIANTS

(71) Applicant: Henkel AG & Co. KGaA, Duesseldorf (DE)

(72) Inventors: Christian Degering, Erkrath (DE); Layla Fernandez, Cologne (DE); Sabine Griemert, Monheim am Rhein (DE); Nina Mussmann, Willich (DE); Inken Prueser, Duesseldorf (DE); Daria Strauss, Duesseldorf (DE); Susanne Wieland, Dormagen/Zons (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 119 days.

(21) Appl. No.: 16/699,013

(22) Filed: Nov. 28, 2019

(65) Prior Publication Data

US 2020/0172890 A1 Jun. 4, 2020

(30) Foreign Application Priority Data

Nov. 29, 2018 (EP) .................................... 18209177

(51) Int. Cl.
*C12N 9/54* (2006.01)
(52) U.S. Cl.
CPC ........ *C12N 9/54* (2013.01); *C12Y 304/21062* (2013.01)
(58) Field of Classification Search
CPC .................................................... C12N 9/6424
See application file for complete search history.

(56) References Cited

U.S. PATENT DOCUMENTS

| 5,340,735 A * | 8/1994 | Christianson ............ C07K 1/00 435/221 |
| 2012/0238005 A1 | 9/2012 | Wieland et al. |
| 2014/0018282 A1 | 1/2014 | Wieland et al. |
| 2014/0227764 A1 | 8/2014 | Hellmuth et al. |
| 2015/0017707 A1* | 1/2015 | Mussmann ........ C11D 3/38654 435/264 |
| 2016/0186159 A1 | 6/2016 | O'Connell et al. |
| 2016/0237418 A1 | 8/2016 | Hellmuth et al. |
| 2017/0037343 A1* | 2/2017 | Hellmuth .................. C12N 9/48 |
| 2017/0175098 A1* | 6/2017 | Pedersen .................. C12N 9/54 |
| 2018/0216040 A1* | 8/2018 | Baltsen .............. C11D 3/38636 |
| 2018/0298368 A1* | 10/2018 | Raab ...................... C11D 3/386 |

FOREIGN PATENT DOCUMENTS

| DE | 102004027091 A1 | 12/2005 |
| EP | 3044302 A1 | 7/2016 |
| WO | 9221760 A1 | 12/1992 |
| WO | 9523221 A1 | 8/1995 |
| WO | 2009121725 A1 | 10/2009 |
| WO | 2011032988 A1 | 3/2011 |
| WO | 2012080202 A1 | 6/2012 |
| WO | 2013060621 A1 | 5/2013 |
| WO | 2015036152 A1 | 3/2015 |
| WO | 2015044206 A1 | 4/2015 |
| WO | 2015055477 A1 | 4/2015 |
| WO | WO 2016/001449 | * 1/2016 |
| WO | 2016096714 A1 | 6/2016 |
| WO | WO-2018011277 A1 * | 1/2018 ......... C11D 11/0017 |
| WO | 2018069158 A1 | 4/2018 |

OTHER PUBLICATIONS

Folz et al., "Substrate Specificity of Eukaryotic Signal Peptidase", J. Biol. Chem., 1988, vol. 263, No. 4, pp. 2070-2078.*
Airaksinen et al., "Modified Base Compositions at Degenerate Positions of a Mutagenic Oligonucleotide Enhance Randomness in Site-Saturation Mutagenesis", Nucleic Acids Research, 1998, vol. 26, No. 2, pp. 576-581.*
Altschul et al., "Gapped BLAST and PSI-BLAST: a new generation of protein database search programs", Nucleic Acids Res., 1997, pp. 3389-3402, vol. 25, No. 17.
Bender et al., "The Determination of the Concentration of Hydrolytic Enzyme Solutions . . . " J. Am. Chem. Soc. 88, 24, 1966, pp. 5890-5913, Dec. 20, 1966.
Search report issued for corresponding EP application No. 18209177.7 dated May 9, 2019, 7 pages, (for information purpose only).
Search report issued for EP application No. 18209175 1 dated Jan. 10, 2019, 7 pages, (for information purpose only).

* cited by examiner

*Primary Examiner* — Suzanne M Noakes
(74) *Attorney, Agent, or Firm* — VIERING JENTSCHURA & PARTNER MBB

(57) ABSTRACT

Proteases may include an amino acid sequence which has at least 70% sequence identity with the amino acid sequence given in SEQ ID NO:1 over its entire length and has (i) one or more first amino acid substitutions at positions corresponding to positions 3, 4, 99, 199, or combinations thereof, and (ii) one or more second amino acid substitutions at positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259, 267, or combinations thereof based on the numbering according to SEQ ID NO:1, and relates to the preparation and use thereof. Proteases of this kind demonstrate very good stability with good cleaning performance.

12 Claims, No Drawings
Specification includes a Sequence Listing.

PERFORMANCE-ENHANCED AND STORAGE STABLE PROTEASE VARIANTS

REFERENCE TO A SEQUENCE LISTING SUBMITTED VIA EFS-WEB

The content of the ASCII text file of the sequence listing named "2018P35177US_P75394_sequencelisting_ST25" which is 3 kb in size was created on Feb. 6, 2020 and electronically submitted via EFS-Web herewith. The sequence listing is incorporated herein by reference in its entirety.

CROSS-REFERENCE TO RELATED APPLICATION

The present application claims priority to European Patent Application Serial No.: 18 209 177.7 according to 35 U.S.C. § 119, which was filed on Nov. 29, 2018; which is incorporated herein by reference in its entirety and for all purposes.

TECHNICAL FIELD

The present invention is in the field of enzyme technology. The invention generally relates to proteases, the amino acid sequences of which, in particular with regard to the use in washing and cleaning agents, in particular with regard to liquid washing and cleaning agents, have been altered to give them a better storage stability and/or to improve their cleaning performance, and also relates to the nucleic acids coding therefor and to the production thereof. The invention further relates to the uses of these proteases and to methods in which they are used, as well as to agents containing them, in particular washing and cleaning agents, in particular liquid washing and cleaning agents.

BACKGROUND

Proteases are some of the technically most important enzymes. They are the longest established enzymes for washing and cleaning agents, and are contained in virtually all modern, effective washing and cleaning agents. They bring about the decomposition of protein-containing stains on the item to be cleaned. Of these, in turn, proteases of the subtilisin type (subtilases, subtilopeptidases, EC 3.4.21.62) are particularly important, which are serine proteases due to the catalytically active amino acids. They act as non-specific endopeptidases and hydrolyze any acid amide bonds that are inside peptides or proteins. Their optimum pH is usually in the distinctly alkaline range. For an overview of this family see, for example, the article "Subtilases: Subtilisin-like Proteases" by R. Siezen, pages 75-95 in "Subtilisin enzymes," edited by R. Bott and C. Betzel, New York, 1996. Subtilases are naturally formed from microorganisms. In particular, the subtilisins formed and secreted by Bacillus species are the most significant group of subtilases.

Examples of the subtilisin proteases used in washing and cleaning agents are the subtilisins BPN' and Carlsberg, the protease PB92, the subtilisins 147 and 309, the alkaline protease from Bacillus lentus, in particular from Bacillus lentus DSM 5483, the subtilisin DY and the enzymes thermitase, proteinase K and proteases TW3 and TW7, which belong to the subtilases but no longer to the subtilisins in the narrower sense, and variants of said proteases having an amino acid sequence that has been altered with respect to the starting protease. Proteases are altered in a targeted manner or randomly using methods known from the prior art, and are thus optimized for use in washing and cleaning agents, for example. This includes point, deletion or insertion mutagenesis, or fusion with other proteins or protein parts. Appropriately optimized variants are therefore known for the majority of proteases known from the prior art.

International patent applications WO95/23221A1 WO92/21760A1 and WO2013/060621A1 disclose variants of the alkaline protease from Bacillus lentus DSM 5483, which are suitable for use in washing or cleaning agents. Furthermore, the international patent application WO2011/032988A1 and the European patent application EP3044302A1 discloses washing and cleaning agents which contain variants of the alkaline protease from Bacillus lentus DSM 5483. The protease variants disclosed in these references may be altered, among other positions, at positions 3, 4, 99 and/or 199, in the alkaline protease counting method of Bacillus lentus DSM 5483 and, for example, having the amino acids 3T, 4I, 99E or 199I at said positions. However, combinations of other changes, as described below, do not emerge from these references.

In general, only selected proteases are suitable for use in liquid, surfactant-containing preparations in any case. Many proteases do not exhibit sufficient catalytic performance in such preparations. For the use of proteases in washing and cleaning agents, therefore, a high catalytic activity under conditions as they are during a wash cycle and a high storage stability is particularly desirable.

Consequently, protease and surfactant-containing liquid formulations from the prior art are disadvantageous in that the proteases contained, under standard washing conditions (e.g. in a temperature range of from 20° C. to 40° C.), do not have satisfactory proteolytic activity or are not sufficiently storage-stable and the formulations therefore do not exhibit optimal cleaning performance on protease-sensitive stains.

SUMMARY

Surprisingly, it has now been found that a protease of the alkaline protease type from Bacillus lentus DSM 5483 or a sufficiently similar protease (based on the sequence identity) which has (i) at least one amino acid substitution, in particular at least one of the amino acid substitutions 3T, 4I, 99E or 199I, at at least one of the positions corresponding to positions 3, 4, 99 or 199, and has (ii) at least one amino acid substitution, in particular at least one amino acid substitution selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C and 267S, at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, in each case based on the numbering according to SEQ ID NO:1, is improved in terms of its storage stability and/or washing performance and/or its stability compared with the wild-type form (SEQ ID NO:1) or a starting variant as described in WO2013060621A1, and is therefore particularly suitable for use in washing or cleaning agents.

A protease may include an amino acid sequence which has at least 70% sequence identity with the amino acid sequence given in SEQ ID NO:1 over its entire length and (i) has at least one amino acid substitution at at least one of the positions corresponding to positions 3, 4, 99 or 199, and (ii) has at least one amino acid substitution at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, in each case based on the numbering according to SEQ ID NO:1.

A method for preparing a protease, as defined above, may include introducing at least one amino acid substitution at (i) at least one of the positions corresponding to positions 3, 4, 99 or 199 based on the numbering according to SEQ ID NO:1, and (ii) at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267 based on the numbering according to SEQ ID NO:1, into a starting molecule which has an amino acid sequence that has at least 70% sequence identity with the amino acid sequence given in SEQ ID NO:1 over its entire length.

A protease within the meaning of the present patent application therefore comprises both the protease as such and a protease prepared by a method. All statements regarding the protease therefore relate both to the protease as such and to the proteases prepared by means of corresponding methods.

Further aspects relate to the nucleic acids coding for these proteases, to non-human host cells containing proteases or nucleic acids, and to agents comprising proteases, in particular washing and cleaning agents, to washing and cleaning methods, and to uses of the proteases in washing or cleaning agents in order to remove protein-containing stains.

These and other aspects, features, and advantages will become apparent to a person skilled in the art through the study of the following detailed description and claims. Any feature from one aspect of the invention can be used in any other aspect of the invention. Furthermore, it will readily be understood that the examples contained herein are intended to describe and illustrate, but not to limit, the invention and that, in particular, the invention is not limited to these examples.

DETAILED DESCRIPTION

Numerical ranges that are indicated in the format "from x to y" also include the stated values. If several preferred numerical ranges are indicated in this format, it is self-evident that all ranges that result from the combination of the various endpoints are also included.

"At least one," as used herein, means one or more, i.e. 1, 2, 3, 4, 5, 6, 7, 8, 9, 10, 11, 12, 13, 14 or more.

"Liquid," as used herein, includes liquids and gels as well as pasty compositions. It is preferred that the liquid compositions are flowable and pourable at room temperature, but it is also possible that they have a yield point.

Amino acid substitutions at the positions described herein result in improved storage stability and/or improved cleaning performance of this modified protease in washing and cleaning agents.

In embodiments, the modification(s) at (i) at least one of the positions corresponding to positions 3, 4, 99 or 199 based on the numbering according to SEQ ID NO:1, and (ii) at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267 based on the numbering according to SEQ ID NO:1, result(s) in improved cleaning performance of this modified protease in washing and cleaning agents on at least one protease-sensitive stain. Proteases therefore allow improved removal of at least one, preferably a plurality of, protease-sensitive stains on textiles and/or hard surfaces, for example crockery.

In embodiments, the modification(s) at (i) at least one of the positions corresponding to positions 3, 4, 99 or 199 based on the numbering according to SEQ ID NO:1, and (ii) at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267 based on the numbering according to SEQ ID NO:1, result(s) in improved storage stability of this modified protease in washing and cleaning agents.

In embodiments of the protease, the protease has (i) at least one amino acid substitution selected from the group consisting of 3T, 4I, 99E or 199I, at at least one of the positions corresponding to positions 3, 4, 99 or 199, and has (ii) at least one amino acid substitution selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C or 267S, at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267.

In embodiments, the protease has (i) at least one amino acid substitution selected from the group consisting of 3T, 4I, 99E or 199I, at at least one of the positions corresponding to positions 3, 4, 99 or 199, and has (ii) at least one amino acid substitution selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C or 267S, at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, the combination of the at least one amino acid substitution from group (i) and the at least one amino acid substitution from group (ii) results in improved cleaning performance of this modified protease in washing and cleaning agents on at least one protease-sensitive stain.

In embodiments, the protease has (i) at least one amino acid substitution selected from the group consisting of 3T, 4I, 99E or 199I, at at least one of the positions corresponding to positions 3, 4, 99 or 199, and has (ii) at least one amino acid substitution selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C or 267S, at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, the combination of the at least one amino acid substitution from group (i) and the at least one amino acid substitution from group (ii) results in improved storage stability of this modified protease in washing and cleaning agents.

In embodiments, the protease has (i) at least one amino acid substitution selected from the group consisting of 3T, 4I, 99E or 199I, at at least one of the positions corresponding to positions 3, 4, 99 or 199, and has (ii) at least one amino acid substitution selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C or 267S, at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, the combination of the at least one amino acid substitution from group (i) and the at least one amino acid substitution from group (ii) results in both improved cleaning performance and improved storage stability of this modified protease in washing and cleaning agents.

Certain embodiments of the proteases have improved storage stability. They have increased stability in washing or cleaning agents in comparison with the wild-type enzyme (SEQ ID NO:1) and in particular also compared with the starting variant of the protease (SEQ ID NO:2 from WO2013/060621A1), in particular when stored for 3 or more days, 4 or more days, 7 or more days, 10 or more days, 12 or more days, 14 or more days, 21 or more days or 28 or more days.

Certain embodiments of the proteases, independently of or in addition to increased storage stability, may also have increased catalytic activity in washing or cleaning agents. In various embodiments, the proteases may have proteolytic activity which, based on the wild type (SEQ ID NO:1) and/or a starting variant of the protease that is already performance-enhanced (SEQ ID NO:2 from WO2013/060621A1), is at least 101%, 102%, 103%, 104%, 105%, 106%, 107%, 108%, 109% or 110%. Such performance-enhanced proteases allow improved washing results on proteolytically sensitive stains in various temperature ranges, in particular in a temperature range of from 20° C. to 40° C.

Furthermore, embodiments of proteases have a special stability in washing or cleaning agents, for example against surfactants and/or bleaching agents and/or chelators and/or against temperature influences, in particular against high temperatures, for example between 50 and 65° C., in particular 60° C., and/or against acidic or alkaline conditions and/or against pH-value changes and/or against denaturing or oxidizing agents and/or against proteolytic degradation and/or against a change in the redox ratios. With particularly embodiments, performance-enhanced and/or more temperature-stable protease variants are therefore provided. With other, more particularly embodiments, performance-enhanced and more temperature-stable protease variants are provided. Such advantageous embodiments of proteases therefore allow for improved washing results on protease-sensitive stains in a wide temperature range.

In the context, cleaning performance is understood to mean the lightening performance on one or more stains, in particular on laundry or crockery. In the context, both the washing or cleaning agent which comprises the protease or the washing or cleaning liquor formed by this agent and the protease itself each have cleaning performance. The cleaning performance of the enzyme thus contributes to the cleaning performance of the agent or of the washing or cleaning liquor formed by the agent. The cleaning performance is determined as indicated below.

Washing liquor is understood to mean the stock solution containing the washing or cleaning agent which acts on textiles or fabric or hard surfaces and thus comes into contact with stains on textiles or fabrics or hard surfaces. Usually, the washing liquor is formed when the washing or cleaning process begins and the washing or cleaning agent is diluted with water, for example in a dishwasher, a washing machine or other suitable container.

The proteases exhibit enzymatic activity, i.e. they are capable of hydrolyzing peptides and proteins, in particular in a washing or cleaning agent. A protease is therefore an enzyme which catalyzes the hydrolysis of amide/peptide bonds in protein/peptide substrates and is thus able to cleave proteins or peptides. Furthermore, a protease is a mature protease, i.e. the catalytically active molecule without signal peptide(s) and/or propeptide(s). Unless stated otherwise, the sequences given also each refer to mature (processed) enzymes.

In various embodiments, the protease is a free enzyme. This means that the protease can act directly with all the components of an agent and, if the agent is a liquid agent, that the protease is in direct contact with the solvent of the agent (e.g. water). In other embodiments, an agent may contain proteases that form an interaction complex with other molecules or that contain a "coating." In this case, an individual protease molecule or multiple protease molecules may be separated from the other constituents of the agent by a surrounding structure. Such a separating structure may arise from, but is not limited to, vesicles such as a micelle or a liposome. The surrounding structure may also be a virus particle, a bacterial cell or a eukaryotic cell. In various embodiments, an agent may include cells of *Bacillus pumilus* or *Bacillus subtilis*, which express the proteases, or cell culture supernatants of such cells.

In various embodiments, the protease comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99% and 99.5% identical to the amino acid sequence given in SEQ ID NO:1 over its entire length and has (i) at least one amino acid substitution at at least one of the positions corresponding to positions 3, 4, 99 or 199, the at least one amino acid substitution being selected from the group consisting of 3T, 4I, 99E or 199I, and has (ii) at least one amino acid substitution at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, the at least one amino acid substitution being selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C and 267S, based on the numbering according to SEQ ID NO:1 in each case.

In embodiments, the protease comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99% and 99.5% identical to the amino acid sequence given in SEQ ID NO:1 over its entire length and has (i) at least two amino acid substitutions at at least two of the positions corresponding to positions 3, 4, 99 or 199, the at least two amino acid substitutions being selected from the group consisting of 3T, 4I, 99E or 199I, and has (ii) at least one amino acid substitution at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, the at least one amino acid substitution being selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C and 267S, based on the numbering according to SEQ ID NO:1 in each case.

In embodiments, the protease comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99% and 99.5% identical to the amino acid sequence given in SEQ ID NO:1 over its entire length and has (i) at least three amino acid substitutions at at least three of the positions corresponding to positions 3, 4, 99 or 199, the at least three amino acid substitutions being selected from the group consisting of 3T, 4I, 99E or 199I, and has (ii) at least one amino acid substitution at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, the at least one amino acid substitution being selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C and 267S, based on the numbering according to SEQ ID NO:1 in each case.

In particularly embodiments, the protease comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99% and 99.5% identical to the amino acid sequence given in SEQ ID NO:1 over its entire length and has (i) the amino acid substitutions 3T, 4I, 99E and 199I, and has (ii) at least one amino acid substitution at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, the at least one amino acid substitution being selected from the group consisting of 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C and 267S, based on the numbering according to SEQ ID NO:1 in each case.

The feature whereby a protease has at least one of the given amino acid substitutions means that it contains one (of the given) amino acid substitution(s) at the relevant position, i.e. at least the given positions are not otherwise mutated or deleted, for example by fragmenting of the protease.

The identity of nucleic acid or amino acid sequences is determined by a sequence comparison. This sequence comparison is based on the BLAST algorithm established and commonly used in the prior art (cf. e.g. Altschul et al. (1990): "Basic local alignment search tool," J. Mol. Biol. 215: 403-410, and Altschul et al. (1997): "Gapped BLAST and PSI-BLAST: a new generation of protein database search programs," Nucleic Acids Res. 25:3389-3402) and in principle occurs by associating similar sequences of nucleotides or amino acids in the nucleic acid or amino acid sequences. A tabular association of the positions concerned is referred to as alignment. Another algorithm available in the prior art is the FASTA algorithm. Sequence comparisons (alignments), in particular multiple sequence comparisons, are created using computer programs. The Clustal series (cf. e.g. Chenna et al. (2003): "Multiple sequence alignment with the Clustal series of programs," Nucleic Acid Res. 31:3497-3500), T-Coffee (cf. e.g. Notredame et al. (2000): "T-Coffee: A novel method for multiple sequence alignments," J. Mol. Biol. 302: 205-217) or programs based on these programs or algorithms are frequently used, for example. Sequence comparisons (alignments) using the computer program Vector NTI® Suite 10.3 (Invitrogen Corporation, 1600 Faraday Avenue, Carlsbad, Calif., USA) with the predetermined, default parameters, and the AlignX module of which for sequence comparisons is based on ClustalW, are also possible. Unless stated otherwise, the sequence identity given herein is determined by the BLAST algorithm.

Such a comparison also allows a statement to be made regarding the similarity of the compared sequences. It is usually given in percent identity, i.e. the proportion of identical nucleotides or amino acid residues in said sequences, or corresponding positions in an alignment. The broader concept of homology takes conserved amino acid exchanges into account in the case of amino acid sequences, i.e. amino acids having similar chemical activity, since they usually perform similar chemical activities within the protein. Therefore, the similarity of the compared sequences may also be stated as percent homology or percent similarity. Identity and/or homology information can be provided regarding whole polypeptides or genes or only regarding individual regions. Homologous or identical regions of different nucleic acid or amino acid sequences are therefore defined by matches in the sequences. Such regions often have identical functions. They can be small and comprise only a few nucleotides or amino acids. Often, such small regions perform essential functions for the overall activity of the protein. It may therefore be expedient to relate sequence matches only to individual, optionally small regions. Unless stated otherwise, however, identity or homology information in the present application relates to the entire length of the particular nucleic acid or amino acid sequence indicated.

The indication that an amino acid position corresponds to a numerically designated position in SEQ ID NO:1 therefore means that the corresponding position is associated with the numerically designated position in SEQ ID NO:1 in an alignment as defined above.

In a further embodiment, the protease is characterized in that the cleaning performance thereof (after storage, e.g. over 3 weeks) is not significantly reduced compared with the wild-type enzyme (SEQ ID NO:1) or a starting variant described in WO201360621A1, i.e. has at least 80% of the reference washing performance, at least 100%, more at least 110% or more. The cleaning performance can be determined in a washing system containing a washing agent in a dosage between 4.5 and 7.0 grams per liter of washing liquor, and the protease, the proteases to be compared being used in the same concentration (based on active protein) and the cleaning performance with respect to a stain on cotton is determined by measuring the degree of cleaning of the washed textiles. For example, the washing process can take place for 60 minutes at a temperature of 40° C. and the water can have a water hardness between 15.5 and 16.5° (German hardness). The concentration of the protease in the washing agent intended for this washing system is 0.001 to 0.1 wt. %, 0.01 to 0.06 wt. %, based on active, purified protein.

A liquid reference washing agent for such a washing system may, for example, be composed as follows (all figures in wt. %): 4.4% alkyl benzene sulfonic acid, 5.6% further anionic surfactants, 2.4% $C_{12}$-$C_{18}$ Na salts of fatty acids (soaps), 4.4% non-ionic surfactants, 0.2% phosphonates, 1.4% citric acid, 0.95% NaOH, 0.01% defoamer, 2% glycerol, 0.08% preservatives, 1% ethanol, and the remainder being demineralized water. The dosage of the liquid washing agent is between 4.5 and 6.0 grams per liter of washing liquor, for example 4.7, 4.9 or 5.9 grams per liter of washing liquor. Washing in a pH range between pH 7 and pH 10.5, such as between pH 7.5 and pH 8.5, may be beneficial.

The cleaning performance is determined for example at 20° C. or 40° C. using a liquid washing agent such as e.g. that stated above, the washing process being carried out for 60 minutes at 600 rpm.

The degree of whiteness, i.e. the lightening of stains, as a measure of the cleaning performance is determined by optical measuring methods, such as photometrically. A suitable device for this purpose is for example the Minolta CM508d spectrometer. Usually, the devices used for the measurement are calibrated beforehand with a white standard, such as a supplied white standard.

A liquid reference hand dishwashing agent for a washing system of this type may be composed, for example, as follows (all figures in wt. %): 8-20% alkyl benzene sulfonic acid, 30-80% demineralized water, 5.4% NaOH (50%), 7.14% fatty alcohol ether sulfate, 2.0% NaCl (20%), 0.383% phosphoric acid ($H_3PO_4$; 34%/85%), 0.1% preservative, 0.25% perfume, 1.0% dye, 0.04% bitter principle.

The activity-equivalent use of the relevant protease ensures that the respective enzymatic properties, for example the cleaning performance on certain stains, are compared even if the ratio of active substance to total protein (the values of the specific activity) diverges. In general, a low specific activity can be compensated for by adding a larger amount of protein.

Otherwise, methods for determining protease activity are well known to, and routinely used by, a person skilled in the art of enzyme technology. For example, such methods are disclosed in Tenside, vol. 7 (1970), p. 125-132. Alternatively, the protease activity can be determined by the release of the chromophore para-nitroaniline (pNA) from the substrate suc-L-Ala-L-Ala-L-Pro-L-Phe-p-Nitroanilide (AAPF). The protease cleaves the substrate and releases pNA. The release of the pNA causes an increase in absorbance at 410 nm, the temporal progression of which is a measure of the enzymatic activity (cf. Del Mar et al., 1979). The measurement is carried out at a temperature of 25° C., a pH of 8.6, and a wavelength of 410 nm. The measuring time is 5 min and the measuring interval is 20 to 60 sec. The protease activity is usually indicated in protease units (PE). Suitable protease activities amount for example to 2.25, 5 or 10 PE per ml of washing liquor, for example. However, the protease activity is not equal to zero.

An alternative test for establishing the proteolytic activity of the proteases is an optical measuring method, such as a photometric method. The appropriate test involves the protease-dependent cleavage of the substrate protein casein. This is cleaved by the protease into a multitude of smaller partial products. The totality of these partial products has an increased absorption at 290 nm compared with uncleaved casein, it being possible for this increased absorption to be determined using a photometer, and thus for a conclusion to be drawn regarding the enzymatic activity of the protease.

The protein concentration can be determined using known methods, for example the BCA method (bicinchoninic acid; 2,2'-bichinolyl-4,4'-dicarboxylic acid) or the Biuret method (Gornall et al., J. Biol. Chem., 177 (1948), p. 751-766). The active protein concentration can be determined in this regard by titrating the active centers using a suitable irreversible inhibitor and determining the residual activity (cf. Bender et al., J. Am. Chem. Soc. 88, 24 (1966), p. 5890-5913).

In addition to the amino acid modifications discussed above, proteases can have other amino acid modifications, in particular amino acid substitutions, insertions or deletions. Such proteases are, for example, further developed by targeted genetic modification, i.e. by mutagenesis methods, and optimized for specific applications or with regard to specific properties (for example with regard to their catalytic activity, stability, etc.). Furthermore, nucleic acids can be introduced into recombination approaches and can thus be used to generate completely novel proteases or other polypeptides.

The aim is to introduce targeted mutations such as substitutions, insertions or deletions into the known molecules in order, for example, to improve the cleaning performance of enzymes. For this purpose, in particular the surface charges and/or the isoelectric point of the molecules and thus their interactions with the substrate can be altered. For instance, the net charge of the enzymes can be altered in order to influence the substrate binding, in particular for use in washing and cleaning agents. Alternatively or in addition, one or more corresponding mutations can increase the stability or catalytic activity of the protease and thus improve its cleaning performance. Advantageous properties of individual mutations, e.g. individual substitutions, can complement one another. A protease which has already been optimized with regard to specific properties, for example with respect to its stability during storage, can therefore also be further developed.

For the description of substitutions relating to exactly one amino acid position (amino acid exchanges), the following convention is used herein: first, the naturally occurring amino acid is designated in the form of the internationally used one-letter code, followed by the associated sequence position and finally the inserted amino acid. Several exchanges within the same polypeptide chain are separated by slashes. For insertions, additional amino acids are named following the sequence position. In the case of deletions, the missing amino acid is replaced by a symbol, for example an asterisk or a dash, or a Δ is indicated before the corresponding position. For example, A95G describes the substitution of alanine at position 95 by glycine, A95AG the insertion of glycine after the amino acid alanine at position 95 and A95* or AA59 the deletion of alanine at position 95. This nomenclature is known to a person skilled in the field of enzyme technology.

A protease may be obtainable from a protease as described above as the starting molecule by one-time or multiple conservative amino acid substitution, the protease in the numbering according to SEQ ID NO:1 having at least one of the above-described amino acid substitutions. The term "conservative amino acid substitution" means the exchange (substitution) of one amino acid residue for another amino acid residue, with this exchange not resulting in a change to the polarity or charge at the position of the exchanged amino acid, e.g. the exchange of a nonpolar amino acid residue for another nonpolar amino acid residue. Conservative amino acid substitutions may include, for example: G=A=S, I=V=L=M, D=E, N=Q, K=R, Y=F, S=T, G=A=I=V=L=M=Y=F=W=P=S=T.

Alternatively or additionally, the protease is characterized in that it is obtainable from a protease as a starting molecule by fragmentation or deletion, insertion or substitution mutagenesis and comprises an amino acid sequence which matches the starting molecule over a length of at least 190, 200, 210, 220, 230, 240, 250, 260, 261, 262, 263, 264, 265, 266, 267, 268 or 269 contiguous amino acids, the protease having (i) at least one amino acid substitution at at least one of the positions that correspond to the positions 3, 4, 99 or 199, and (ii) at least one amino acid substitution at at least one of the positions that correspond to the positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267.

For instance, it is possible to delete individual amino acids at the termini or in the loops of the enzyme without the proteolytic activity being lost or diminished in the process. Furthermore, such fragmentation or deletion, insertion or substitution mutagenesis can also for example reduce the allergenicity of the enzymes concerned and thus improve their overall applicability. Advantageously, the enzymes retain their proteolytic activity even after mutagenesis, i.e. their proteolytic activity corresponds at least to that of the starting enzyme, i.e. in an embodiment the proteolytic activity is at least 80%, such as at least 90% of the activity of the starting enzyme. Other substitutions can also exhibit advantageous effects. Both single and multiple contiguous amino acids can be exchanged for other amino acids.

The amino acid positions are in this case defined by an alignment of the amino acid sequence of a protease with the amino acid sequence of the protease from Bacillus lentus, as given in SEQ ID NO:1. Furthermore, the assignment of the positions depends on the mature protein. This assignment is also to be used in particular if the amino acid sequence of a protease comprises a higher or lower number of amino acid residues than the protease from Bacillus lentus according to SEQ ID NO:1. Proceeding from the above-mentioned positions in the amino acid sequence of the protease from Bacillus lentus, the modification positions in a protease are those which are assigned to precisely these positions in an alignment.

Advantageous positions for sequence alterations, in particular substitutions, of the protease from Bacillus lentus, which are of particular significance when transferred to homologous positions of the proteases and which impart advantageous functional properties to the protease are therefore the positions which correspond to the positions described herein in an alignment, i.e. in the numbering according to SEQ ID NO:1. At the positions mentioned, the following amino acid residues are present in the wild-type molecule of the protease from Bacillus lentus (SEQ ID NO: 1): S3, V4, S9, L21, N42, R44, R99, I105, A112, G113, A131, V137, S139, T141, V145, I159, A168, Q176, N177, S182, V193, N198, V199, P204, G205, S206, S210, N212, Q230, S234, S250, S253, N255, S259.

Further confirmation of the correct assignment of the amino acids to be modified, i.e. in particular their functional correspondence, can be provided by comparative experiments, according to which the two positions assigned to one another on the basis of an alignment are modified in the same way in both compared proteases, and observations are made as to whether the enzymatic activity is modified in the same way in both cases. If, for example, an amino acid exchange in a specific position of the protease from Bacillus lentus according to SEQ ID NO:1 is accompanied by a modification of an enzymatic parameter, for example an increase in the KM value, and a corresponding modification of the enzymatic parameter, for example likewise an increase in the KM value, is observed in a protease variant of which the amino acid exchange has been achieved by the same introduced amino acid, this can therefore be considered to be confirmation of the correct assignment.

All of these aspects are also applicable to the method for preparing a protease. Accordingly, a method further comprises one or more of the following method steps:

(a) Introducing a single or multiple conservative amino acid substitution into the protease, the protease having:
  i) at least one amino acid substitution at at least one of the positions corresponding to positions 3, 4, 99 or 199, and
  ii) at least one amino acid substitution at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267;

(b) Modifying the amino acid sequence by fragmentation or deletion, insertion or substitution mutagenesis such that the protease comprises an amino acid sequence which matches the starting molecule over a length of at least 190, 200, 210, 220, 230, 240, 250, 260, 261, 262, 263, 264, 265, 266, 267, 268 or 269 contiguous amino acids, the protease having:
  i) at least one amino acid substitution at at least one of the positions corresponding to positions 3, 4, 99 or 199, and
  ii) at least one amino acid substitution at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267.

All embodiments also apply to the method.

In further embodiments, the protease or the protease prepared by means of a method is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99% or 99.5% identical to the amino acid sequence given in SEQ ID NO:1 over its entire length. The protease or the protease prepared using a method has (i) at least one amino acid substitution 3T, 4I, 99E or 199I at at least one of the positions corresponding to positions 3, 4, 99 or 199, and has (ii) at least one amino acid substitution 9C, 21F, 21W, 42S, 42H, 44S, 105V, 112V, 113A, 131D, 137I, 139R, 141S, 145I, 159L, 168V, 176E, 177D, 182C, 193M, 198D, 204L, 205D, 206A, 210C, 212D, 230E, 234A, 250N, 253C, 255Y, 259C or 267S at at least one of the positions corresponding to positions 9, 21, 42, 44, 105, 112, 113, 131, 137, 139, 141, 145, 159, 168, 176, 177, 182, 193, 198, 204, 205, 206, 210, 212, 230, 234, 250, 253, 255, 259 or 267, in each case based on the numbering according to SEQ ID NO:1. Examples of this are the following amino acid substitution variants: (i) S3T+V4I+R99E+V199I+A267S+N255Y; (ii) S3T+V4I+R99E+V199I+N198D+S234A+L21F; (iii) S3T+V4I+R99E+V199I+N212D; (iv) S3T+V4I+R99E+V199I+G205D; (v) S3T+V4I+R99E+V199I+S182C; (vi) S3T+V4I+R99E+V199I+R44S+S234A; (vii) S3T+V4I+R99E+V199I+S253C; (viii) S3T+V4I+R99E+V199I+I105V; (ix) S3T+V4I+R99E+V199I+N177D; (x) S3T+V4I+R99E+V199I+V193M; (xi) S3T+V4I+R99E+V199I+S9C; (xii) S3T+V4I+R99E+V199I+N198D; (xiii) S3T+V4I+R99E+V199I+S259C; (xiv) S3T+V4I+R99E+V199I+I159L+Q230E; (xv) S3T+V4I+R99E+V199I+P204L; (xvi) S3T+V4I+R99E+V199I+L21F; (xvii) S3T+V4I+R99E+V199I+N42H; (xviii) S3T+V4I+R99E+V199I+S139R+S250N; (xix) S3T+V4I+R99E+V199I+N42S; (xx) S3T+V4I+R99E+V199I+V137I; (xxi) S3T+V4I+R99E+V199I+V145I; (xxii) S3T+V4I+R99E+V199I+S206A; (xxiii) S3T+V4I+R99E+V199I+G113A+L21W; (xxiv) S3T+V4I+R99E+V199I+A112V; (xxv) S3T+V4I+R99E+V199I+A168V; (xxvi) S3T+V4I+R99E+V199I+Q176E+A131D; (xxvii) S3T+V4I+R99E+V199I+T141S+S210C, in each case based on the numbering according to SEQ ID NO: 1, and the variants described in the examples.

The protease may also be stabilized, in particular by one or more mutations, for example substitutions, or by coupling to a polymer. An increase in stability during storage and/or during use, for example in the washing process, leads to longer enzymatic activity and thus improves the cleaning performance. In principle, all stabilization options which are described in the prior art and/or are appropriate are considered. Those stabilizations that are achieved by mutations of the enzyme itself do not require any further work steps following the recovery of the enzyme. Examples of sequence modifications suitable for this purpose are mentioned above. Further suitable sequence modifications are known from the prior art.

Further possibilities for stabilization are, for example:
Modifying the binding of metal ions, in particular the calcium binding sites, for example by exchanging one or more of the amino acids involved in the calcium binding with one or more negatively charged amino acids and/or by introducing sequence modifications into at least one of the chains of the two amino acids arginine/glycine;
Protecting against the influence of denaturing agents such as surfactants by mutations that cause a modification of the amino acid sequence on or at the surface of the protein;
Exchanging amino acids near the N-terminus with those likely to contact the rest of the molecule via non-covalent interactions, thus contributing to the maintenance of the globular structure.

Non-limiting embodiments are those in which the enzyme is stabilized in several ways, as several stabilizing mutations act additively or synergistically.

A protease may have at least one chemical modification. A protease with such an alteration is referred to as a derivative, i.e. the protease is derivatized.

In the context of the present application, derivatives are thus understood to mean those proteins of which the pure amino acid chain has been chemically modified. Such derivatizations can be achieved, for example, in vivo by the host cell that expresses the protein. In this regard, couplings of low-molecular-weight compounds such as lipids or oligosaccharides are particularly noteworthy. However, the derivatizations may also be carried out in vitro, for example by the chemical conversion of a side chain of an amino acid or by covalent bonding of another compound to the protein. For example, it is possible to couple amines to carboxyl groups of an enzyme in order to alter the isoelectric point. Another such compound may also be another protein that is bound to a via bifunctional chemical compounds, for example. Derivatization is also understood to mean the covalent bonding to a macromolecular carrier or a non-covalent inclusion in suitable macromolecular cage structures. Derivatizations may, for example, affect the substrate specificity or bonding strength to the substrate or cause a temporary blockage of the enzymatic activity when the coupled substance is an inhibitor. This can be expedient, for example, for the period of the storage. Such modifications may further affect the stability or enzymatic activity. They can also be used to reduce the allergenicity and/or immunogenicity of the protein and thus, for example, increase its skin compatibility. For example, couplings with macromolecular compounds, for example polyethylene glycol, can improve the protein in terms of stability and/or skin compatibility.

Derivatives of a protein can also be understood in the broadest sense to mean preparations of these proteins. Depending on the recovery, processing or preparation, a protein can be combined with various other substances, for example from the culture of the producing microorganisms. A protein may also have been deliberately added to other substances, for example to increase its storage stability. Therefore, all preparations of a protein may be used. This is also irrespective of whether or not it actually exhibits this enzymatic activity in a particular preparation. This is because it may be desired that it has no or only low activity during storage, and exhibits its enzymatic function only at the time of use. This can be controlled via appropriate accompanying substances, for example. In particular, the joint preparation of proteases with specific inhibitors is possible in this regard.

Of all the proteases or protease variants and/or derivatives described above, those of which the storage stability and/or the cleaning performance is improved compared with the starting variant is beneficial, the cleaning performance being determined in a washing system as described above.

A nucleic acid may code for a protease, as well as to a vector containing such a nucleic acid, in particular a cloning vector or an expression vector.

These may be DNA or RNA molecules. They can be present as a single strand, as a single strand that is complementary to this single strand, or as a double strand. In particular in the case of DNA molecules, the sequences of the two complementary strands must be taken into account in all three possible reading frames. Furthermore, it should be noted that different codons, i.e. base triplets, can code for the same amino acids such that a particular amino acid sequence can be coded by a plurality of different nucleic acids. Due to this degeneracy of the genetic code, all of the nucleic acid sequences which can code any of the proteases described above are included. A person skilled in the art is able to determine these nucleic acid sequences unequivocally since, despite the degeneracy of the genetic code, defined amino acids can be assigned to individual codons. Therefore, a person skilled in the art proceeding from an amino acid sequence can easily determine nucleic acids coding for said amino acid sequence. Furthermore, in the case of nucleic acids, one or more codons may be replaced by synonymous codons. This aspect relates in particular to the heterologous expression of the enzymes. For instance, every organism, for example a host cell of a production strain, has a particular codon usage. Codon usage is understood to mean the translation of the genetic code into amino acids by the relevant organism. Bottlenecks can occur in the protein biosynthesis if the codons on the nucleic acid in the organism are faced with a comparatively small number of loaded tRNA molecules. Although coding for the same amino acid, this results in a codon being translated less efficiently in the organism than a synonymous codon coding for the same amino acid. Due to the presence of a higher number of tRNA molecules for the synonymous codon, it can be translated more efficiently in the organism.

Using methods which are currently generally known, such as chemical synthesis or the polymerase chain reaction (PCR), in conjunction with molecular-biological and/or protein-chemical standard methods, it is possible for a person skilled in the art to prepare the corresponding nucleic acids and even complete genes on the basis of known DNA and/or amino acid sequences. Such methods are known for example from Sambrook, J., Fritsch, E F and Maniatis, T. 2001. Molecular cloning: a laboratory manual, 3. Edition Cold Spring Laboratory Press.

Vectors are understood to mean elements consisting of nucleic acids, which elements contain a nucleic acid as the characteristic nucleic acid region. They are able to establish these as a stable genetic element in a species or cell line over several generations or cell divisions. Vectors are special plasmids, i.e. circular genetic elements, in particular when used in bacteria. A nucleic acid may be cloned into a vector. The vectors include, for example, those originating from bacterial plasmids, viruses or bacteriophages, or predominantly synthetic vectors or plasmids with elements of a wide variety of origins. With the additional genetic elements present in each case, vectors are able to establish themselves as stable units in the corresponding host cells over several generations. They may be present as separate units in an extrachromosomal manner or integrated into a chromosome or chromosomal DNA.

Expression vectors comprise nucleic acid sequences which enable them to replicate in the host cells containing them, such as microorganisms, i.e bacteria, and to express a contained nucleic acid there. The expression is in particular influenced by the promoter(s) that regulate the transcription. In principle, the expression can take place by the natural promoter originally located before the nucleic acid to be expressed, but also by a promoter of the host cell provided on the expression vector or also by a modified or completely different promoter of another organism or another host cell. In the present case, at least one promoter is provided for the expression of a nucleic acid and used for the expression thereof. Furthermore, expression vectors can be regulatable, for example by changing the cultivation conditions or when a specific cell density of the host cells containing them is reached or by addition of specific substances, in particular activators of gene expression. An example of such a substance is the galactose derivative isopropyl-β-D-thiogalactopyranoside (IPTG), which is used as an activator of the bacterial lactose operon (lac operon). In contrast with expression vectors, the nucleic acid contained is not expressed in cloning vectors.

A non-human host cell which contains a nucleic acid or a vector or which contains a protease, in particular one which secretes the protease into the medium surrounding the host cell. A nucleic acid or a vector is transformed into a microorganism, which then represents a host cell. Alternatively, individual components, i.e. nucleic acid parts or fragments of a nucleic acid can be introduced into a host cell such that the resulting host cell contains a nucleic acid or a vector. This procedure is particularly suitable when the host cell already contains one or more constituents of a nucleic acid or a vector and the further constituents are then supplemented accordingly. Methods for transforming cells are established in the prior art and are well known to a person skilled in the art. In principle, all cells, i.e. prokaryotic or eukaryotic cells, are suitable as host cells. The host cells may be managed in a genetically advantageous manner, for example in terms of the transformation with the nucleic acid or the vector and the stable establishment thereof, for example unicellular fungi or bacteria. Furthermore, host cells are characterized by good microbiological and biotechnological manageability. This relates, for example, to easy cultivation, high growth rates, low requirements for fermentation media and good production and secretion rates for foreign proteins. Non-limiting host cells secrete the (transgenically) expressed protein into the medium surrounding the host cells. Furthermore, the proteases can be modified by the cells producing them after their production, for example by attachment of sugar molecules, formylations, aminations, etc. Such post-translational modifications can functionally influence the protease.

Other embodiments are those host cells of which the activity can be regulated on account of genetic regulatory elements, which are, for example, made available on the vector but may also be present in these cells from the outset. These host cells may be induced to express for example by the controlled addition of chemical compounds which are used as activators, by modifying the cultivation conditions, or upon reaching a specific cell density. This enables economical production of the proteins. An example of such a compound is IPTG, as described above.

Prokaryotic or bacterial cells may be used as host cells. Bacteria are characterized by short generation times and low demands on cultivation conditions. As a result, cost-effective cultivation methods or preparation methods can be established. In addition, a person skilled in the art has a wealth of experience in the case of bacteria in fermentation technology. For a specific production, gram-negative or gram-positive bacteria may be suitable for a wide variety of reasons to be determined experimentally in individual cases, such as nutrient sources, product formation rate, time requirement, etc.

In the case of gram-negative bacteria, such as *Escherichia coli*, a large number of proteins are secreted into the periplasmic space, i.e. into the compartment between the two membranes enclosing the cells. This may be advantageous for particular applications. Furthermore, gram-negative bacteria can also be designed such that they eject the expressed proteins not only into the periplasmic space, but into the medium surrounding the bacterium. In contrast, gram-positive bacteria such as bacilli or actinomycetes or other representatives of Actinomycetales have no outer membrane, and therefore secreted proteins are released immediately into the medium surrounding the bacteria, usually the nutrient medium, from which the expressed proteins can be purified. They can be isolated directly from the medium or further processed. In addition, gram-positive bacteria are related or identical to most of the origin organisms for technically significant enzymes and usually even form comparable enzymes, meaning that they have a similar codon usage and the protein synthesizer is naturally aligned accordingly.

Host cells may be altered in terms of their requirements for the culture conditions, may have different or additional selection markers or may express other or additional proteins. In particular, this may also involve those host cells which transgenically express several proteins or enzymes.

The present invention is applicable in principle to all microorganisms, in particular to all fermentable microorganisms, particularly those of the genus *Bacillus*, and leads to it being possible to produce proteins by the use of such microorganisms. Such microorganisms then represent host cells.

In a further embodiment, the host cell is characterized in that it is a bacterium, such as one selected from the group of the genera of *Escherichia, Klebsiella, Bacillus, Staphylococcus, Corynebacterium, Arthrobacter, Streptomyces, Stenotrophomonas* and *Pseudomonas*, i.e. one selected from the group of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacte-* rium glutamicum, Arthrobacter oxidans, Streptomyces lividans, Streptomyces coelicolor and Stenotrophomonas maltophilia.

The host cell may also be a eukaryotic cell, however, which is characterized in that it has a cell nucleus. A host cell is characterized in that it has a cell nucleus. In contrast with prokaryotic cells, eukaryotic cells are capable of post-translationally modifying the protein formed. Examples thereof are fungi such as actinomycetes or yeasts such as Saccharomyces or Kluyveromyces. This can be particularly advantageous, for example, if the proteins are to undergo specific modifications in connection with their synthesis that make such systems possible. Modifications carried out by eukaryotic systems, in particular in connection with the protein synthesis, include, for example, the binding of low-molecular-weight compounds such as membrane anchors or oligosaccharides. Such oligosaccharide modifications may be desirable, for example, to lower the allergenicity of an expressed protein. Co-expression with the enzymes naturally formed by such cells, such as cellulases, may be advantageous. Furthermore, for example, thermophilic fungal expression systems may be particularly suitable for the expression of temperature-resistant proteins or variants.

The host cells are cultivated and fermented in the conventional way, for example in discontinuous or continuous systems. In the first case, a suitable nutrient medium is inoculated with the host cells and the product is harvested from the medium after a period to be determined experimentally. Continuous fermentations are characterized by the achievement of a flow equilibrium, in which cells partially die over a comparatively long period of time but also grow back and the protein formed can be removed from the medium at the same time.

Host cells may be used to prepare proteases. A method for preparing a protease may include:
 a) cultivating a host cell, and
 b) Isolating the protease from the culture medium or from the host cell.

The method may include fermentation processes. Fermentation processes are known per se from the prior art and represent the actual large-scale production step, usually followed by a suitable purification method of the prepared product, for example the proteases. All fermentation processes which are based on a corresponding method for preparing a protease constitute embodiments of this subject matter.

Fermentation processes which are characterized in that the fermentation is carried out via a feed strategy shall be considered in particular. In this case, the media components that are consumed by the continuous cultivation are added. As a result, considerable increases can be achieved both in the cell density and in the cell mass or dry mass and/or in particular in the activity of the protease of interest. Furthermore, the fermentation can also be designed in such a way that undesired metabolic products are filtered out or neutralized by adding buffers or suitable counter ions.

The protease prepared can be harvested from the fermentation medium. Such a fermentation process is better than isolation of the protease from the host cell, i.e. product preparation from the cell mass (dry matter), but requires the provision of suitable host cells or one or more suitable secretion markers or mechanisms and/or transport systems for the host cells to secrete the protease into the fermentation medium. Without secretion, the protease can alternatively be isolated from the host cell, i.e. purified from the cell mass, for example by precipitation with ammonium sulphate or ethanol, or by chromatographic purification.

All of the above-mentioned aspects can be combined into methods in order to prepare protease.

An agent is characterized in that it contains a protease as described above. The agent may be a washing or cleaning agent.

This subject matter covers all conceivable types of washing or cleaning agents, both concentrates and undiluted agents, for use on a commercial scale, in washing machines or for hand washing or cleaning. These include washing agents for textiles, carpets, or natural fibers, for which the term washing agent is used. These include, for example, dishwashing detergents for dishwashers or manual dishwashing detergents or cleaners for hard surfaces such as metal, glass, porcelain, ceramics, tiles, stone, painted surfaces, plastics, wood or leather, for which the term cleaning agent is used, i.e. in addition to manual and mechanical dishwashing detergents, also, for example, scouring agents, glass cleaners, WC toilet scenters, etc. The washing and cleaning agents also include auxiliary washing agents which are added to the actual washing agent during manual or automatic textile washing in order to achieve a further effect. Furthermore, washing and cleaning agents also include textile pre-treatment and post-treatment agents, i.e. those agents with which the item of laundry is brought into contact before the actual washing cycle, for example to loosen stubborn soiling, and also those agents which give the laundry further desirable properties such as a pleasant feel, crease resistance or low static charge in a step subsequent to the actual textile wash. Inter alia, softeners are included in the last-mentioned agents.

The washing or cleaning agents, which may be in the form of powdered solids, in further-compacted particulate form, as gels, homogeneous solutions or suspensions, may contain, in addition to a protease, all known ingredients conventional in such agents, with at least one other ingredient being present in the agent. The agents may in particular contain surfactants, builders, peroxygen compounds or bleach activators. They may also contain water-miscible organic solvents, further enzymes, sequestering agents, electrolytes, pH regulators and/or further auxiliaries such as optical brighteners, graying inhibitors, foam regulators, as well as dyes and fragrances, and combinations thereof.

In particular, a combination of a protease with one or more further ingredients of the agent is advantageous, since, in embodiments, such an agent has improved cleaning performance by virtue of resulting synergisms. In particular, combining a protease with a surfactant and/or a builder and/or a peroxygen compound and/or a bleach activator can result in such a synergism. However, in embodiments, the agent may not contain boric acid.

Advantageous ingredients of agents are disclosed in international patent application WO2009/121725A1, starting at the penultimate paragraph of page 5 and ending after the second paragraph on page 13. Reference is expressly made to this disclosure and the disclosure therein is incorporated in the present patent application by reference.

An agent advantageously contains the protease in an amount of from 2 µg to 20 mg, such as from 5 µg to 17.5 mg, i.e. from 20 µg to 15 mg, and for example from 50 µg to 10 mg per g of the agent. In various embodiments, the concentration of the protease (active enzyme) described herein in the agent is >0 to 1 wt. %, such as 0.001 to 0.1 wt. %, based on the total weight of the agent or composition. Further, the protease contained in the agent, and/or other ingredients of the agent, may be coated with a substance which is impermeable to the enzyme at room temperature or in the absence of water, and which becomes permeable to the enzyme under conditions of use of the agent. Such an embodiment is thus characterized in that the protease is coated with a substance which is impermeable to the protease at room temperature or in the absence of water. Furthermore, the washing or cleaning agent itself may be packaged in a container, such as an air-permeable container, from which it is released shortly before use or during the washing process.

In further embodiments, the agent is characterized in that it (a) is present in solid form, in particular as a flowable powder having a bulk density of from 300 g/l to 1200 g/l, in particular from 500 g/l to 900 g/l, or (b) is present in pasty or liquid form, and/or (c) is present in the form of a gel or in the form of dosing pouches, and/or (d) is present as a single-component system, or (e) is divided into a plurality of components.

These embodiments include all solid, powdered, liquid, gel or pasty administration forms of agents, which may optionally also consist of a plurality of phases and can be present in compressed or uncompressed form. The agent may be present as a flowable powder, in particular having a bulk density of from 300 g/l to 1200 g/l, in particular from 500 g/l to 900 g/l or from 600 g/l to 850 g/l. The solid administration forms of the agent also include extrudates, granules, tablets or pouches. Alternatively, the agent may also be in liquid, gel or pasty form, for example in the form of a non-aqueous liquid washing agent or a non-aqueous paste or in the form of an aqueous liquid washing agent or a water-containing paste. Liquid agents may be used. The agent may also be present as a one-component system. Such agents consist of one phase. Alternatively, an agent may also consist of a plurality of phases. Such an agent is therefore divided into a plurality of components.

Washing or cleaning agents may contain only one protease. Alternatively, they may also contain other hydrolytic enzymes or other enzymes in a concentration that is expedient for the effectiveness of the agent. A further embodiment is therefore represented by agents which further comprise one or more further enzymes. Further enzymes which can be used are all enzymes which can exhibit catalytic activity in the agent, in particular a lipase, amylase, cellulase, hemicellulase, mannanase, tannase, xylanase, xanthanase, xyloglucanase, ß-glucosidase, pectinase, carrageenase, perhydrolase, oxidase, oxidoreductase or another protease, which may be different from the proteases, as well as mixtures thereof. Further enzymes are advantageously contained in the agent in an amount of from $1 \times 10^{-8}$ to 5 wt. % based on active protein. Each further enzyme is contained in agents in an amount of from $1 \times 10^{-7}$ to 3 wt. %, from 0.00001 to 1 wt. %, from 0.00005 to 0.5 wt. %, from 0.0001 to 0.1 wt. %, and from 0.0001 to 0.05 wt. %, based on active protein in each case. The enzymes exhibit synergistic cleaning performance against specific stains or spots, i.e. the enzymes contained in the agent composition support one another in their cleaning performance. There is such synergism between the protease contained and a further enzyme of an agent, including in particular between said protease and an amylase and/or a lipase and/or a mannanase and/or a cellulase and/or a pectinase. Synergistic effects can arise not only between different enzymes, but also between one or more enzymes and other ingredients of the agent.

In the cleaning agents described herein, the enzymes to be used may furthermore be formulated together with accompanying substances, for example from fermentation. In liquid formulations, the enzymes are used as enzyme liquid formulations.

The enzymes are generally not provided in the form of pure protein, but rather in the form of stabilized, storable and transportable preparations. These ready-made preparations include, for example, the solid preparations obtained through granulation, extrusion, or lyophilization or, particularly in the case of liquid or gel agents, solutions of the enzymes, advantageously maximally concentrated, low-water, and/or supplemented with stabilizers or other auxiliaries.

Alternatively, the enzymes can also be encapsulated, for both the solid and the liquid administration form, for example by spray-drying or extrusion of the enzyme solution together with a natural polymer or in the form of capsules, for example those in which the enzymes are enclosed in a set gel, or in those of the core-shell type, in which an enzyme-containing core is coated with a water-, air-, and/or chemical-impermeable protective layer. In the case of overlaid layers, other active ingredients, such as stabilizers, emulsifiers, pigments, bleaching agents, or dyes, can be additionally applied. Such capsules are applied using inherently known methods, for example by shaking or roll granulation or in fluid bed processes. Such granules are advantageously low in dust, for example due to the application of polymeric film-formers, and stable in storage due to the coating.

Moreover, it is possible to formulate two or more enzymes together, such that a single granule exhibits a plurality of enzyme activities.

The enzymes can also be incorporated in water-soluble films, such as those used in the formulation of washing and cleaning agents in a unit dosage form. Such a film allows the release of the enzymes following contact with water. As used herein, "water-soluble" refers to a film structure that is completely water-soluble. Such a film consists of (fully or partially hydrolyzed) polyvinyl alcohol (PVA).

A method for cleaning textiles or hard surfaces is disclosed, which is characterized in that an agent is used in at least one method step, or in that a protease becomes catalytically active in at least one method step, in particular such that the protease is used in an amount of from 40 µg to 4 g, such as from 50 µg to 3 g, for example from 100 µg to 2 g, i.e. from 200 µg to 1 g, or in the concentrations described herein.

In various embodiments, the method described above is characterized in that the protease is used at a temperature of from 0 to 100° C., such as 0 to 60° C., for example 20 to 40° C., i.e. at 25° C.

These include both manual and mechanical methods. Methods for cleaning textiles are generally characterized by the fact that, in a plurality of method steps, various cleaning-active substances are applied to the material to be cleaned and washed off after the exposure time, or in that the material to be cleaned is otherwise treated with a washing agent or a solution or dilution of this agent. The same applies to methods for cleaning all materials other than textiles, in particular hard surfaces. All conceivable washing or cleaning methods can be enhanced in at least one of the method steps by the use of a washing or cleaning agent or a protease, and then represent embodiments. All aspects, objects, and embodiments described for the protease and agents containing it are also applicable to this subject matter. Therefore, reference is expressly made at this point to the disclosure at the appropriate point with the note that this disclosure also applies to the above-described method.

Since proteases naturally already have hydrolytic activity and also exhibit this in media which otherwise have no cleaning power, for example in a simple buffer, a single and/or the sole step of such a method can consist in a protease, which is the only cleaning-active component, being brought into contact with the stain, such as in a buffer solution or in water. This represents a further embodiment of this subject matter.

Alternative embodiments of this subject matter are also represented by methods for treating textile raw materials or for textile care, in which a protease becomes active in at least one method step. Among these, methods for textile raw materials, fibers or textiles with natural components may be used, such as those with wool or silk.

Finally, proteases described herein may be used in washing or cleaning agents, for example as described above, for the (improved) removal of protein-containing stains, for example from textiles or hard surfaces. In embodiments of this use, the protease in the washing or cleaning agent is stored for 3 or more days, 4 or more days, 7 or more days, 10 or more days, 12 or more days, 14 or more days, 21 or more days or 28 or more days before a washing or cleaning process.

All aspects, objects, and embodiments described for the protease and agents containing it are also applicable to this subject matter. Therefore, reference is expressly made at this point to the disclosure at the appropriate point with the note that this disclosure also applies to the above-described use.

EXAMPLES

Example 1: Overview of the Mutations

A subtilisin-type alkaline protease from *Bacillus lentus* is discussed. From a starting variant (protease according to SEQ ID NO:2 from WO2013/060621A1), variants were produced by random mutagenesis, which were then screened, inter alia for improved washing performance and/or enzyme stability. In this way, 27 mutants having improved storage stability and/or improved cleaning performance were generated from said protease.

| Variant | Amino acid substitutions relative to SEQ ID NO: 1 | | | | | |
|---|---|---|---|---|---|---|
| Starting variant | S3T | V4I | R99E | V199I | | |
| Mutant 1 | S3T | V4I | R99E | V199I | A267S | N255Y |
| Mutant 2 | S3T | V4I | R99E | V199I | N198D | S234A | L21F |
| Mutant 3 | S3T | V4I | R99E | V199I | N212D | | |
| Mutant 4 | S3T | V4I | R99E | V199I | G205D | | |
| Mutant 5 | S3T | V4I | R99E | V199I | S182C | | |
| Mutant 6 | S3T | V4I | R99E | V199I | R44S | S234A | |
| Mutant 7 | S3T | V4I | R99E | V199I | S253C | | |
| Mutant 8 | S3T | V4I | R99E | V199I | I105V | | |
| Mutant 9 | S3T | V4I | R99E | V199I | N177D | | |
| Mutant 10 | S3T | V4I | R99E | V199I | V193M | | |
| Mutant 11 | S3T | V4I | R99E | V199I | S9C | | |
| Mutant 12 | S3T | V4I | R99E | V199I | N198D | | |
| Mutant 13 | S3T | V4I | R99E | V199I | S259C | | |
| Mutant 14 | S3T | V4I | R99E | V199I | I159L | Q230E | |
| Mutant 15 | S3T | V4I | R99E | V199I | P204L | | |
| Mutant 16 | S3T | V4I | R99E | V199I | L21F | | |
| Mutant 17 | S3T | V4I | R99E | V199I | N42H | | |
| Mutant 18 | S3T | V4I | R99E | V199I | S139R | S250N | |
| Mutant 19 | S3T | V4I | R99E | V199I | N42S | | |
| Mutant 20 | S3T | V4I | R99E | V199I | V137I | | |
| Mutant 21 | S3T | V4I | R99E | V199I | V145I | | |
| Mutant 22 | S3T | V4I | R99E | V199I | S206A | | |
| Mutant 23 | S3T | V4I | R99E | V199I | G113A | L21W | |
| Mutant 24 | S3T | V4I | R99E | V199I | A112V | | |
| Mutant 25 | S3T | V4I | R99E | V199I | A168V | | |
| Mutant 26 | S3T | V4I | R99E | V199I | Q176E | A131D | |
| Mutant 27 | S3T | V4I | R99E | V199I | T141S | S210C | |

Washing Agent Matrix Used

| Chemical name | wt. % of active substance in the |
|---|---|
| Demineralized water | Remainder |
| Na-LAS | 3-8 |
| Anionic surfactants | 4-6 |
| Sodium lareth | 2.0 |
| Non-ionic surfactants | 2-6 |
| Phosphonate | 0.2-0.6 |
| Citric acid | 0.2-2 |
| NaOH | 1-4 |
| Defoamer | <1 |
| Glycerol | 0.5-2 |
| Preservative | <0.1 |

Without opt. brighteners, perfume, dye and enzymes.
Dosage: 6 g/l

Dishwashing Agent Matrix Used

| Chemical name | wt. % of active substance in the |
|---|---|
| Alkyl benzene sulfonic acid | 8-20 |
| Water | 30-80 |
| NaOH (50%) | 5.4 |
| Fatty alcohol ether sulfate | 7.14 |
| NaCl solution (20%) | 2.0 |
| Phosphoric acid ($H_3PO_4$) | 0.383 (34%) |
| Preservative | 0.1 |
| Perfume | 0.25 |
| Dye | 1.0 |
| Bitter principle | 0.04 |

Example 2: Determination of Storage Stability

Storage

The protease variants were expressed in *Bacillus subtilis*. From the supernatants of the *Bacillus subtilis* culture, the proteases were diluted to an equal level of activity. To determine the storage stability in washing agents or dishwashing agents, 50% washing agent matrix without boric acid or 50% dishwashing agent matrix was added to 50% of appropriately diluted *Bacillus subtilis* culture and mixed well. The sealed vessels were each stored at 40° C. for three or 3.5 weeks. The amount of sample removed was dissolved for 20 minutes at room temperature in 0.1M Tris/HCl (pH 8.6) by stirring. The AAPF assay was then carried out as described below.

Protease Activity Assay

The activity of the protease is determined by the release of the chromophore para-nitroaniline from the substrate succinyl alanine-alanine-proline-phenylalanine-para-nitroanilide (AAPFpNA; Bachem L-1400). The release of the pNA causes an increase in absorbance at 410 nm, the temporal progression of which is a measure of the enzymatic activity.

The measurement was carried out at a temperature of 25° C., a pH of 8.6, and a wavelength of 410 nm. The measuring time was 5 minutes with a measuring interval of from 20 to 60 seconds.

Measurement Approach:

10 µl AAPF solution (70 mg/ml)

1000 µl Tris/HCl (0.1 M, pH 8.6 with 0.1% Brij 35)

10 µl diluted protease solution

Kinetics created over 5 min at 25° C. (410 nm)

In the following, the improved stability is set out in % compared with the stability of the starting variant after storage for 3 weeks at 40° C. in the above-mentioned washing agent or dishwashing agent matrix:

| Variant | Improved stability (%) in the above-mentioned washing agent matrix | Improved stability (%) in the above-mentioned dishwashing agent matrix |
| --- | --- | --- |
| Starting variant | 0 | 0 |
| Mutant 1 | +44 | +14 |
| Mutant 2 | +49 | +55 |
| Mutant 3 | +93 | +41 |
| Mutant 4 | +57 | +5 |
| Mutant 5 | +80 | +11 |
| Mutant 6 | +58 | +15 |
| Mutant 7 | +9 | +41 |
| Mutant 8 | +102 | +58 |
| Mutant 9 | +65 | +52 |
| Mutant 10 | +43 | +35 |
| Mutant 11 | +67 | +25 |
| Mutant 12 | +60 | +19 |
| Mutant 13 | +54 | +28 |
| Mutant 14 | +64 | +9 |
| Mutant 15 | +56 | +16 |
| Mutant 16 | +59 | +0 |
| Mutant 17 | +64 | +22 |
| Mutant 18 | +42 | +2 |
| Mutant 19 | +46 | +29 |
| Mutant 20 | +58 | +4 |
| Mutant 21 | +73 | +12 |
| Mutant 22 | +63 | +33 |
| Mutant 23 | +71 | +22 |
| Mutant 24 | +47 | +5 |
| Mutant 25 | +38 | +24 |
| Mutant 26 | +68 | +62 |
| Mutant 27 | +77 | +48 |

All the variants demonstrate improved stability in washing agents and/or dishwashing agents in comparison with the starting variant.

Example 3: Determination of Cleaning Performance

Mini Washing Test

Washing test with *Bacillus subtilis* culture supernatants containing the screened protease mutants by heterologous expression. The supernatants are used in washing agents in the equivalent activity to the benchmark=starting variant at a market-standard concentration for proteases. Unlike the determination of storage stability, the samples are not stored, but the cleaning performance is determined directly. The mutants are all based on the washing performance of the starting variant, which is set to be equal to 100% (sum of the 7 stains, corrected by the performance of the washing agent alone).

Conditions: 40° C., 16° dH water, 1h

Stains:

1. CFT CS038
2. CFT PC-10
3. WfK 10N
4. CFT C-03
5. EMPA 112
6. CFT C-05
7. H-MR-B

Punched-out pieces of fabric (diameter=10 mm) were placed in microtiter plates, washing liquor was preheated to 40° C., final concentration 3.17 g/l, the liquor and enzyme were added to the soiling, were incubated for 1 hour at 40° C. and 600 rpm, then the stain was rinsed several times with clear water, allowed to dry and the brightness was determined using a colorimeter. The lighter the fabric, the better the cleaning performance. The L value=brightness is measured here, the higher the brighter. The sum of the 7 stains is given in % based on the starting variant corrected by the performance of the washing agent without protease.

| Variant | Performance in the washing test at 40° C. |
| --- | --- |
| Starting variant | 100% |
| Mutant 10 | 104% |
| Mutant 13 | 104% |

Variants 10 and 13 demonstrate increased washing performance in comparison with the starting variant.

Proteases, in particular variants 10 and 13, therefore demonstrate not only improved storage stability but also improved cleaning performance.

What is claimed is:

1. A protease comprising an amino acid sequence having at least 70% sequence identity to SEQ ID NO:1, wherein the protease comprises: i) first amino acid substitutions at at least four positions corresponding to positions 3, 4, 99, and 199; wherein the amino acid substitutions are S3T, V4I, R99E, and V199T; and ii) one or more second amino acid substitutions at positions corresponding to positions A267S+N255Y; N198D+S234A+L21F; N212D; G205D; S182C; R44S+S234A; 253C; I105V; N177D; S9C; N198D; S259C; I159L+Q230E; P204L; L21F; S139R+S250N; N42S; V137I; V145I; S206A; G113A+L21W; A112V; A168V; Q176E+A131D; or T1418+S210C.

2. The protease according to claim 1 further comprising:
   (a) single or multiple conservative amino acid substitution; or
   (b) fragmentation or deletion, insertion, substitution, or mutagenesis.

3. The protease according to claim 1, wherein the one or more second amino acid substitutions comprise one of the following substitutions selected from the group consisting of N212D, S182C, I105V, and T141S+S210C.

4. The protease according to claim 1, wherein the protease comprises the one or more second amino acid substitutions at positions corresponding to positions A267S+N255Y; N198D+S234A+L21F; G205D; R44S+S234A; S253C; I105V; N177D; N198D; S259C; I159L+Q230E; P204L; L21F; S139R+S250N; V137I; V145I; S206A; G113A+L21W; A112V; A168V; Q176E+A131D; or T141S+S210C.

5. The protease according to claim 1, wherein the protease has at least 95% sequence identity to SEQ ID NO: 1.

6. A washing agent composition or cleaning agent composition comprising at least one protease according to claim 1.

7. A method for preparing a protease comprising an amino acid sequence having at least 70% sequence identity to SEQ ID NO: 1 and having first and second amino acid substitutions, comprising: (i) introducing first amino acid substitutions at at least four positions corresponding to positions 3, 4, 99, 199, wherein the amino acid substitutions are S3T, V4I, R99E, and V199T; and (ii) introducing one or more second amino acid substitutions at positions corresponding to positions A267S+N255Y; N198D+S234A+L21F; N212D; G205D; S182C; R44S+S234A; 253C; I105V; N177D; S9C; N198D; S259C; I159L+Q230E; P204L; L21F; S139R+S250N; N42S; V137I; V145I; S206A; G113A+L21W; A112V; A168V; Q176E+A131D; or T1418+S210C.

8. The method according to claim 7, further comprising modifying the amino acid sequence by fragmentation or deletion, insertion or substitution mutagenesis such that the protease comprises an amino acid sequence that matches the starting molecule over a length of at least 190 contiguous amino acids.

9. A nucleic acid coding for a protease according to claim 1.

10. A vector containing a nucleic acid according to claim 9.

11. A non-human host cell that contains a vector according to claim 10.

12. A method for preparing a protease, comprising:
a) cultivating a host cell according to claim 11 in a culture medium; and
b) isolating the protease from the culture medium or from the host cell.

* * * * *

SEQUENCE LISTING

<160> NUMBER OF SEQ ID NOS: 1

<210> SEQ ID NO 1
<211> LENGTH: 269
<212> TYPE: PRT
<213> ORGANISM: Bacillus lentus

<400> SEQUENCE: 1

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60
```

```
His Val Ala Gly Thr Ile Ala Ala Leu Asn Asn Ser Ile Gly Val Leu
65              70              75              80

Gly Val Ala Pro Ser Ala Glu Leu Tyr Ala Val Lys Val Leu Gly Ala
                85              90              95

Asp Gly Arg Gly Ala Ile Ser Ser Ile Ala Gln Gly Leu Glu Trp Ala
            100             105             110

Gly Asn Asn Gly Met His Val Ala Asn Leu Ser Leu Gly Ser Pro Ser
        115             120             125

Pro Ser Ala Thr Leu Glu Gln Ala Val Asn Ser Ala Thr Ser Arg Gly
    130             135             140

Val Leu Val Val Ala Ala Ser Gly Asn Ser Gly Ala Ser Ser Ile Ser
145             150             155             160

Tyr Pro Ala Arg Tyr Ala Asn Ala Met Ala Val Gly Ala Thr Asp Gln
                165             170             175

Asn Asn Asn Arg Ala Ser Phe Ser Gln Tyr Gly Ala Gly Leu Asp Ile
            180             185             190

Val Ala Pro Gly Val Asn Val Gln Ser Thr Tyr Pro Gly Ser Thr Tyr
        195             200             205

Ala Ser Leu Asn Gly Thr Ser Met Ala Thr Pro His Val Ala Gly Ala
    210             215             220

Ala Ala Leu Val Lys Gln Lys Asn Pro Ser Trp Ser Asn Val Gln Ile
225             230             235             240

Arg Asn His Leu Lys Asn Thr Ala Thr Ser Leu Gly Ser Thr Asx Leu
            245             250             255

Tyr Gly Ser Gly Leu Val Asn Ala Glu Ala Ala Thr Arg
            260             265
```